United States Patent [19]

Federsel et al.

[11] Patent Number: 5,468,876
[45] Date of Patent: Nov. 21, 1995

[54] INTERMEDIATES FOR THE STEREOCONSERVATIVE SYNTHESIS OF 1-SUBSTITUTED (S)-AND (R)-2-AMINOMETHYLPYRROLIDINES

[75] Inventors: Hans-Jügen Federsel, Stockholm; Thomas Hö, åkarp; Sten I. Rämsby, Södertälje; Peter H. E. Ström, Veberöd, all of Sweden

[73] Assignee: Aktiebolaget Astra, Sodertalje, Sweden

[21] Appl. No.: 203,985

[22] Filed: Feb. 24, 1994

Related U.S. Application Data

[62] Division of Ser. No. 974,683, Nov. 12, 1992, Pat. No. 5,300,660, which is a continuation of Ser. No. 561,278, Aug. 1, 1990, abandoned, which is a continuation of Ser. No. 364,074, Jun. 8, 1989, abandoned, which is a continuation-in-part of Ser. No. 141,605, Dec. 30, 1987, abandoned.

[30] Foreign Application Priority Data

May 22, 1986 [SE] Sweden .................................. 8602339

[51] Int. Cl.[6] ............................................. C07D 207/09
[52] U.S. Cl. ............................................ 548/535; 548/537
[58] Field of Search ................................... 548/535, 537

[56] References Cited

FOREIGN PATENT DOCUMENTS 2452482  3/1979  France .

OTHER PUBLICATIONS

Mohrle, H et al, "*Oxidativer Abbau der N–Methylnicotone*" Arch. Pharm vol 309 (1976) pp. 380–385.
Moragues, J. et al, *J.C.S. Perkins Trans I*, (1976) pp. 938–940.

Krefeli, F. et al, *Arch. Pharm*, vol 316, (1983) pp. 773–781.

Primary Examiner—Jacqueline Haley
Attorney, Agent, or Firm—White & Case

[57] ABSTRACT

Disclosed are (R)- and (S)-isomers of the compounds of the Formulas II and III with at least 95% optical purity

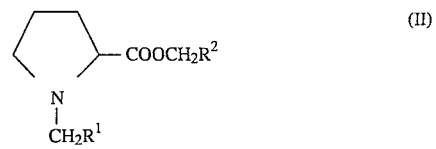

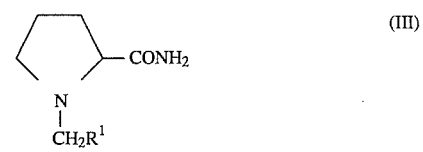

wherein $R^1$ and $R^2$ are the same or different and represent a hydrogen atom, a lower alkyl, lower alkenyl or lower alkynyl group, a cycloalkyl group or a group $(CH_2)_m$ Ph, wherein m is 0–3 and Ph is a substituted or unsubstituted phenyl group.

These compounds are intermediates in the stereoconservative synthesis of 1-substituted (S)- and (R)-2-aminomethylpyrrolidines.

8 Claims, No Drawings

INTERMEDIATES FOR THE STEREOCONSERVATIVE SYNTHESIS OF 1-SUBSTITUTED (S)-AND (R)-2-AMINOMETHYLPYRROLIDINES

CROSS-REFERENCE TO RELATED APPLICATIONS

This application is a divisional of application Ser. No. 07/974,683, filed Nov. 12, 1992, now U.S. Pat. No. 5,300,660, which is a continuation of application Ser. No. 07/561,278, filed Aug. 1, 1990 (abandoned), which is a continuation of application Ser. No. 07/364,074, filed Jun. 8, 1989 (abandoned), which is a continuation-in-part of application Ser. No. 07/141,605, filed Dec. 30, 1987 (abandoned).

FIELD OF THE INVENTION

The present invention relates to a new method for preparation of the (R)-isomer or (S)-isomer of 1-substituted 2-aminomethylpyrrolidines of the formula

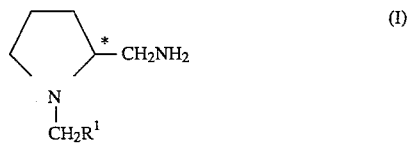

(I)

which may be used as intermediates in the manufacturing of drugs, especially antipsychotics and antiemetics of the substituted benzamide type and to new intermediates prepared.

BACKGROUND OF THE INVENTION

Two principal ways have been used to obtain the enantiomerically pure S-form of the amine of the formula I and R-form of the amine of the formula I, i.e. resolution of racemic amine of the formula I and stereocontrolled synthesis of the optically active amine of the formula I from a chiral starting material. The resolution procedures are described in GB 1 207 752 and AU 526 077 but they involve substantial loss of material and the requirement of often expensive resolving agents. The most attractive procedures rely upon the stereocontrolled conversion of a suitable chiral compound.

Stereocontrolled syntheses have been disclosed by Synthelabo in GB 1 555 890 and by Ravizza in GB 2 014 990.

The procedures of Synthelabo start with the S-form or R-form of proline (Scheme 1), S-form or R-form of glutamic acid or S-form or R-form of prolinol. The procedures cover compounds of the formula I with different $R^a$-groups such as alkyl, cycloalkyl and substituted phenyl. The preferred method using the S-form or the R-form of proline as starting material is a four step synthesis consisting of esterification, aminolysis, acylation and reduction as outlined in Scheme 1. No yields or optical purities besides optical rotations are disclosed.

Scheme 1

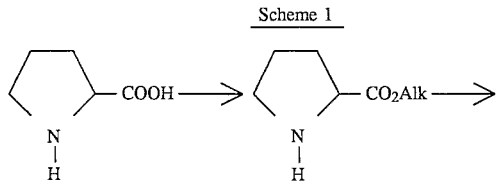

-continued
Scheme 1

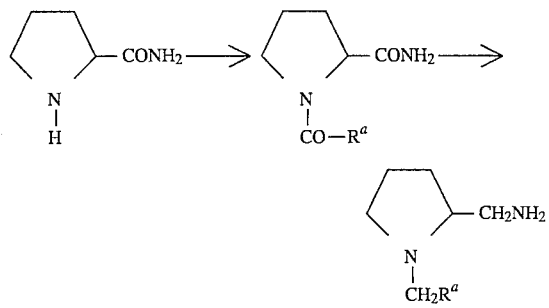

The procedure starting from the S-form or R-form of glutamic acid is a six step synthesis involving condensation, hydrogenation, cyclization, esterification, aminolysis and reduction. No yields are reported.

The Ravizza patent describes a method of preparing the (S)-2-amino-methyl- 1-ethyl-pyrrolidine (the compound of the formula I wherein $R^1=CH_3$) in four steps involving acetylation, reduction, chlorination and amination as outlined in Scheme 2. The crude amine obtained in ca 35% yield from proline is not characterized but converted to sulpiride and purified as such.

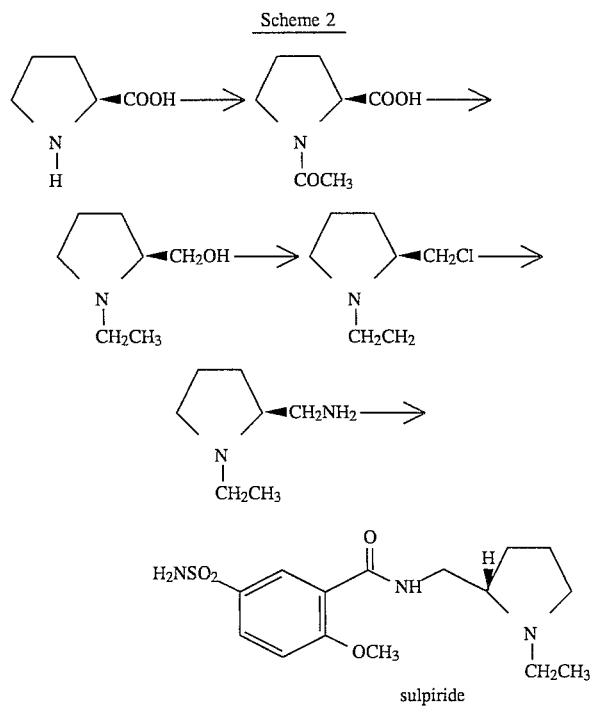

sulpiride

N-alkylation of L-proline with retention of the stereochemistry is described in Beilstein, E III/IV 22, Syst. No. 3244, p. 23–24.

The denoted compounds in the reaction schemes are described in the above-mentioned prior art citations.

1-methyl-2-pyrrolidinecarboxamide prepared from L-proline is described in the European Patent Application 0121244. In Arch. Pharm. 309 (5), p. 380–85 (1976) is described the preparation of methyl(-)-1-methyl-2-pyrrolidinecarboxylate from (–)-proline by N-alkylation followed by O-alkylation. Arch. Pharm 316 (9), p. 771–81 (1983) indicates manufacture of a 1-substituted phenyl methyl-2-pyrrolidinecarboxylate from methyl L-proline by N-alkylation.

DISCLOSURE OF THE INVENTION

The present invention is related to a process for preparation of the (R)- or (S)-isomers of 1-substituted 2-aminomethylpyrrolidines of the formula

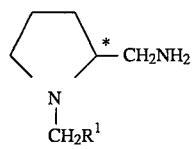  (I)

The process according to the present invention involves a short and efficient synthesis starting from either of the enantiomers of proline. The synthesis from (S)-proline will produce the (S)-isomer of 1-substituted 2-aminomethylpyrrolidines of the formula

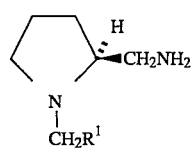  (S)-I and (R)-proline will produce the (R)-isomer of 1-substituted 2-aminomethylpyrrolidines of the formula

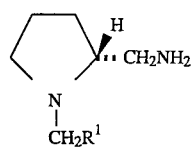  (R)-I

The new process is generally applicable for 2-aminomethylpyrrolidines containing a wide variety of substituents in the 1-position.

$R^1$ in the formulas I, (S)-I and (R)-I above may have the following meaning:

$R^1$ is a hydrogen atom, a saturated or unsaturated lower alkyl group, a cycloalkyl group, or a group $(CH_2)_m$ Ph wherein m is 0–3 and Ph is a phenyl group or a substituted phenyl group; preferably where m is 0;

Saturated lower alkyl groups in the formulas are straight or branched alkyl groups with 1 to 4 carbon atoms, e.g. methyl, ethyl, n-propyl, n-butyl and i-butyl;

Unsaturated lower alkyl groups in the formulas are lower alkenyl groups having straight or branched hydrocarbon chains with 2 to 3 carbon atoms and a double bond, e.g. vinyl, allyl or isopropenyl, or lower alkynyl groups having hydrocarbon chains with 2 to 3 carbon atoms with a triple bond, that is —C≡CH, —CH$_2$—C≡CH and —C≡CCH$_3$;

Cycloalkyl groups in the formulas are unsubstituted 3-6 membered cyclomethylene groups

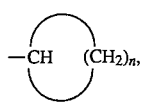

wherein n is 2–5.

Substituted phenyl in the formulas is a phenyl group substituted by for example one or more halo groups such as fluoro, chloro, bromo, trifluoromethyl, lower alkyl such as methyl, ethyl, hydroxy, methoxy or ethoxy in the ortho, meta or para positions, or substituted by methylenedioxy.

In the process of the present invention the preparation proceeds in three steps involving O,N-dialkylation, aminolysis and reduction as shown in Reaction Schemes 3–6. The reactions are performed with full control and retention of the stereochemistry, i.e. stereoconservative. The overall yield from proline is high and the amines of the formulas (S)-I and (R)-I are obtained with very high optical purities. The wording 'an optical pure compound' in the present invention means material containing at least 95% (S)- or (R)-isomer. L-proline is the same as (S)-proline, D-proline is the same as (R)-proline.

Reaction Scheme 3

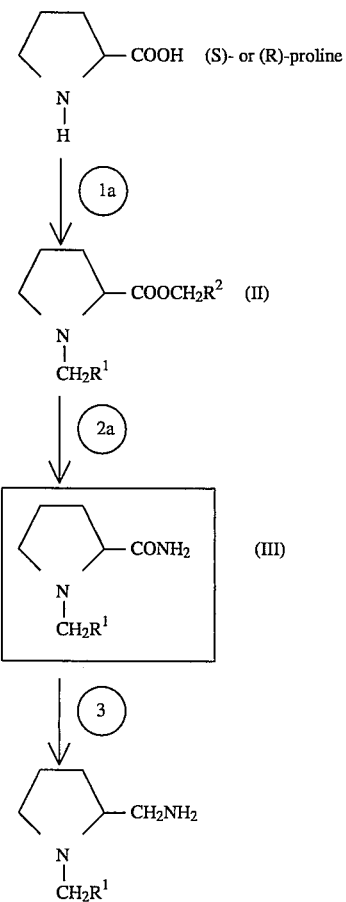

$R^2$ is identical to $R^1$ as defined above.

Reaction Scheme 4

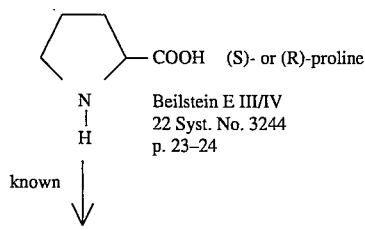

-continued
Reaction Scheme 4
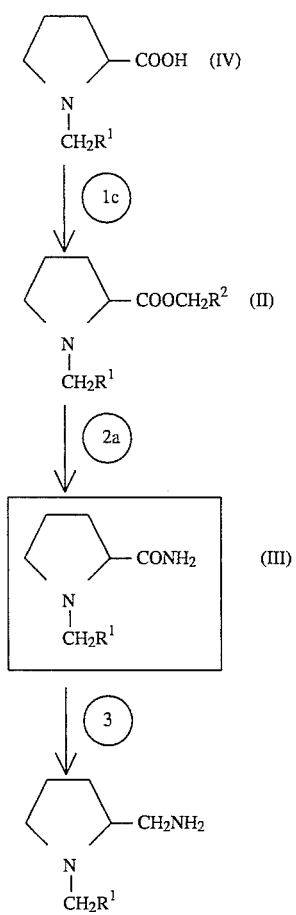
$R^2$ is defined as $R^1$ above and $R^1$ and $R^2$ may be the same or different.
Reaction Scheme 5
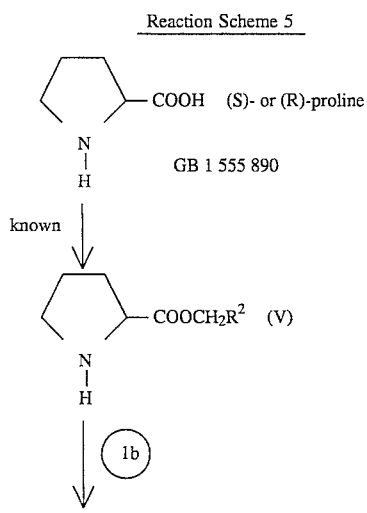
-continued
Reaction Scheme 5
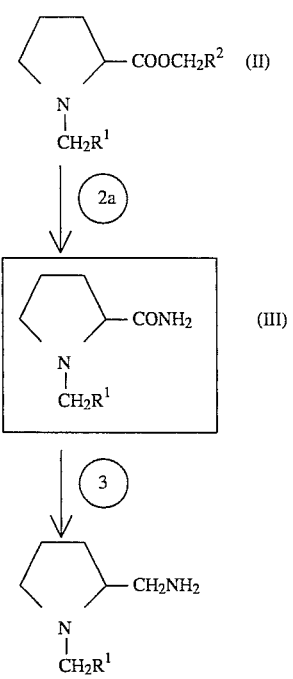
$R^2$ is defined as $R^1$ above and $R^1$ and $R^2$ may be the same or different.
Reaction Scheme 6
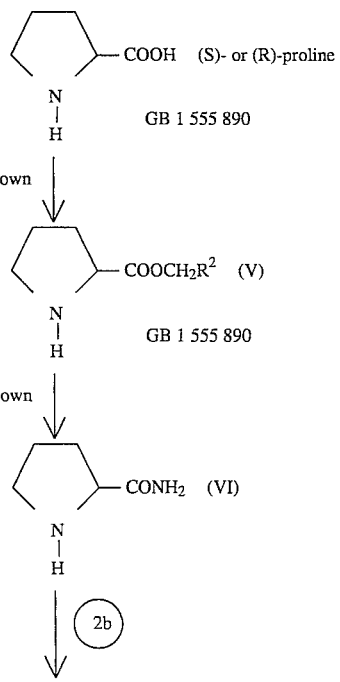

-continued
Reaction Scheme 6

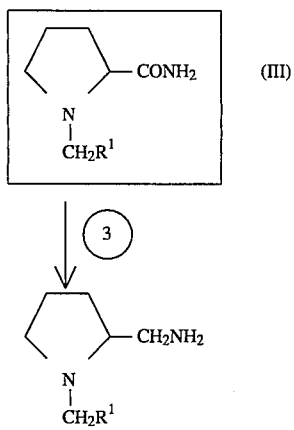

$R^2$ is defined as $R^1$ above and $R^1$ and $R^2$ may be the same or different.

The reaction steps are described in more detail in the following.

Step 1. O,N-dialkylation

Step 1 involves a O,N-dialkylation of (S)- and (R)-proline giving the chiral ester of the formula II in optically pure form. This reaction can be performed directly, without isolation of any intermediate monoalkylation product, giving the compound of formula II, wherein $R^1=R^2$. Alternatively, the reaction can be done as a stepwise monoalkylation involving isolation of an intermediate N-alkylated product

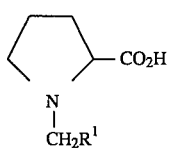

or O-alkylated product

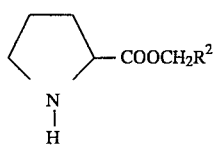

which subsequently are converted to the chiral ester of the formula II, wherein $R^1$ and $R^2$ may be identical or different.

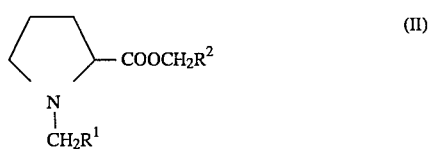

The synthesis of the compounds of the formulas IV and V are known in the art. However, the overall stereoconservative conversion of (S)- or (R)-proline to the chiral ester of the formula II represents a new and efficient process. In this reaction step the pyrrolidine nitrogen is directly converted to a N-alkylated intermediate. Thus, avoiding the stepwise acylation-reduction sequence described in the Synthelabo and Ravizza procedures in Schemes 1 and 2, respectively.

Step 1a. Direct O,N-dialkylation

Direct O,N-dialkylation with $R^1CH_2X$, wherein X is a leaving group for instance a halogen group such as chlorine (—Cl), bromine (—Br), or a sulfonic acid residue such as toluenesulfonyl (—OTs) or methansulfonyl (—OMs).

The reaction is carried out in a suitable solvent such as dimethylformamid (DMF), dimethylsulfoxid (DMSO), hexamethylphosphoric triamid (HMPT), dichloromethane, trichloromethane, ethanol or acetone in presence of a suitable organic or inorganic base such as $CO_3^{2-}$, $OH^-$, $F^-$, tetramethylpiperidine, trialkylamin, 1,5-diazabicyclo [4,3,0] non-5-ene (DBN) or 1,8-diazabicyclo ]4,3,0] undec-7-ene (DBU) without or with a catalyst like iodine ($I^-$) or a phase-transfer catalyst such as quaternary ammonium salts (e.g. $Bu_4 N^+HSO_4$) and crown ethers (e.g. 18-crown-6) with or without polymer support.

Stepwise alkylation

Step 1b. O-alkylation by known methods such as esterification of (R)- or (S)-proline with $R^2CH_2OH$ and acid catalyst such as hydrogen chloride, thionylchloride or by reaction of a reactive proline derivative such as prolylchloride hydrochloride with $R^2CH_2OH$ or by alkylation with $R^2CH_2X$ to give the known intermediate of the formula V followed by N-alkylation by known methods such as reductive alkylation with the corresponding aldehyde $R^1CHO$ and a reducing agent such as $NaBH_3CN$, HCOOH or H2-Pd/C in conventional solvents or alkylation with $R^1CH_2X$ as described in Step 1a to give the (R)- or (S)-isomer of the compound of the formula II. $R^1$, $R^2$ and X are defined as above.

Step 1c. N-alkylation by known methods such as reductive alkylation of (S)- or (R)-proline with the corresponding aldehyde $R^1CHO$ and a reducing agent such as $NaBH_3CN$, HCOOH or $H_2$—Pd/C or alkylation with $R^1CH_2X$ to give the intermediate of the formula IV followed by O-alkylation with $R^2CH_2X$ as performed in Step 1a or with $R^2CH_2OH$ as performed in step 1b. $R^1$, $R^2$ and X are defined as above.

The reaction temperature in the direct O,N-dialkylation step as well as the stepwise monoalkylation steps is below the boiling point of the used solvent, preferably below 50° C.

Step 2a. Aminolysis

Step 2a involves aminolysis of the (R)- or (S)-isomer of the ester of the formula II producing the amide of the formula III by conventional procedures such as reaction with ammonia in hydroxylic solvents or by reaction with $Me_2AlNH_2$. The reaction can preferably be done in an alcoholic ammonia solution at elevated temperature in a pressure bottle or at lower temperature at atmospheric pressure. The reaction can be done without or with a suitable catalyst such as inorganic salt and especially preferred anions are iodide and cyanide. Cyanide being most preferred. The reaction should be carried out at temperatures below 100° C. The racemization diminishes with decreasing temperature and is practically eliminated at about 50° C., which is the preferred temperature for optimal conditions.

Step 2b. N-alkylation

N-alkylation of the known amide of the formula VI in optically pure form by known methods such as reductive alkylation with the corresponding aldehyde $R^1CHO$ and a reducing agent such as NaBH3CN, HCOOH or $H_2$—Pd/C or alkylation with $R^1CH_2^X$, wherein X is a leaving group, e.g. a halogen or a sulfonic acid residue such as —Cl, —Br, —OTs or —OMs to give a (R)- or (S)-isomer of the compound of the formula III. The N-alkylation is performed under the same reaction conditions as described in Step 1a.

Step 3. Reduction

The reduction of the (R)- or (S)-isomer of the amide III can be performed using a hydride reagent such as $LiAlH_4$ $NaBH_4$ with or without addition of a catalyst e.g. $AlCl_3$, BF$_3$, TiCl$_4$, COCl$_2$, CH$_3$COOH and CF$_3$COOH or metal hydride complexes such as NaAlH$_2$(OCH$_2$CH$_2$OCH$_3$ [(CH$_3$)$_2$CHCH$_2$]$_2$AlH, NaBH$_2$S$_3$ or borane and borane complexes such as B$_2$H$_6$ and BH$_3$ S(CH$_3$)$_2$.

These reductions are made at 0° C. to reflux temperature in inert solvents such as hydrocarbons e.g. benzene, toluene, ethers or cyclic ethers such as diethyl ether, tetrahydrofuran (THF), dioxane and glymes.

The amides can also be reduced by catalytic hydrogenation procedures at elevated temperature and pressure using catalysts such as copper chromite in solvents such as dioxane.

The reduction can be performed by conversion of the amides to reactive intermediates such as imino ethers, imino chlorides, nitriles using e.g. (C$_2$H$_5$)$_3$OBF$_4$, PCl$_5$, POCl$_3$ or dehydrating agents in inert solvents e.g CH$_2$Cl$_2$. These intermediates are preferably not isolated but reduced directly with hydride reagents or metals e.g. Zn in alcoholic solvents.
Intermediates Some of the intermediates or starting materials mentioned above and the preparation thereof are known. However, certain intermediates are novel and constitute a further aspect of the invention. Thus, in one aspect the invention is related to novel (R)- or (S)- compounds of the formula

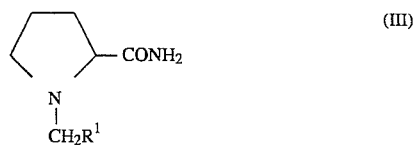

as well as to salts of said compounds, wherein R$^1$ is defined as above, and to the methods for preparing said compounds. The (R)- or (S)-isomers of the compounds of the formula III with at least 95% optical purity is the particularly preferred embodiment of the present invention. Especially preferred (R)- and (S)-isomers of the compounds of the invention with formula III are those wherein R$^1$ is methyl, ethyl, cyclopropyl, vinyl or halophenyl, particularly 4-fluorophenyl.

Also the (R)- or (S)-isomers of the formula II with at least 95% optical purity

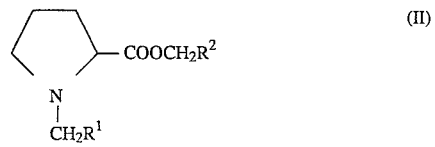

wherein R$^1$ and R$^2$ are the same or different and represent a hydrogen atom, a saturated or unsaturated lower alkyl group, a cycloalkyl group, or a group (CH$_2$)$_m$Ph wherein m is 0–3 and Ph is an unsubstituted or substituted phenyl group with the proviso that when R$^2$ is hydrogen then R$^1$ and R$^2$ are different and with the further proviso that when R$^2$ is hydrogen and R$^1$ is a group (CH$_2$)$_m$Ph, wherein m is O then Ph is unsubstituted or substituted with one or more groups selected from halo, trifluoromethyl, hydroxy, lower alkyl, ethoxy or methylendioxy, and salts of said compounds constitute a further aspect of the invention. Especially preferred compounds are those wherein R$^1$ is methyl, ethyl, cyclopropyl, vinyl or halophenyl, particularly 4-fluorophenyl.
Salts Acceptable salts of compounds of the invention are prepared by methods known in the art. The salts are novel compounds and comprise a further aspect of the invention. Metal salts can be prepared by reacting a metal hydroxide with an acidic compound of the invention. Examples of metal salts which can be prepared in this way are salts containing Li$^+$, Na$^+$, K$^+$ and Ca$^{2+}$. A less soluble metal salt can be precipitated from a solution of a more soluble salt by addition of a suitable metal compound. Also amine salts eg. trialkylamine or onium salts eg. Bu$_4$N$^+$, Ph$_3$p$^+$ can be prepared. Acid salts can be prepared by treating a compound of the invention with an acid such as HCl, HBr, H$_2$SO$_4$, or an organic sulphonic acid, carboxylic acid, phenols such as picric acid.

The invention will in the following be illustrated by means of a number of working examples without being limited thereto.

WORKING EXAMPLES

Example 1. Ethyl (–)-(S)-1-ethyl-2-pyrrolidinecarboxylate

1A. Ethyl iodide (80.3 ml, 1 mol) was added dropwise to a stirred suspension of L-proline (57.5 g, 0.5 mol) and K$_2$CO$_3$ (138 g, 1 mol) in 500 ml of dry dimethylformamide (DMF) for 3 h at room temperature. Stirring was continued overnight. The reaction mixture was poured on ice-water and extracted with ether. The combined ether layers was washed several times with water and dried with brine and MgSO$_4$. The solvent was evaporated under reduced pressure at 50° C. leaving light yellow oil. Distillation of the crude product gave 60.6 g (71%) of the title ester.

Bp 85°–87° C./15 mm [α]$_D^{25}$=–88° (c=0.6, CHCl$_3$) The purity was checked by GLC analysis and was found to be 95%. MS (EI, 70 eV): m/z (rel.int) 171(M, 1.1%), 98(100%), 70(11%)

1B. L-Proline (11.5 g, 0.10 mol), K$_2$CO$_3$ (27.6 g, 0.20 mol) and NaI (4.5 g, 0.03 mol) were mixed in 100 ml dry DMF. Bromoethane (27.2 g, 0.25 mol) was added dropwise for 45 min to the stirred slurry at 30° C. The stirring was continued for 25 h at 30° C. The reaction mixture was poured into 300 ml water and extracted with Et$_2$O (3×100 ml). The combined organic phases were washed with water, dried (MgSO$_4$) and evaporated to give 12.3 g (66%) of the crude title ester (92% purity according to GLC).

GC-MS (EI, 70 eV) studies during the reaction revealed the presence of the two mono-ethylated intermediates, i.e. ethyl 2-pyrrolidinecarboxylate having MS: m/z (rel.int.) 143(M, 1.3%), 70(M—CO$_2$Et, 100%) and 1-ethyl-2pyrrolidinecarboxylic acid having MS: m/z (rel.int.) 98(M—CO$_2$H, 100%).

1C. The example 1B was repeated with the only exception that DMF containing ca 1% water was used as solvent. The same work-up gave 11.1 g (60%) crude title ester having 92% purity.

1D. Bromoethane (3.3 g, 31 mmol) was added to a mixture of ethyl (S)-2-pyrrolidinecarboxylate hydrochloride (5.0 g, 28 mmol), K$_2$CO$_3$ (7.7 g, 56 mmol), triethylamine (0.14 g, 1.4 mmol) and 50 ml acetonitrile at room temperature for 30 min. The stirring was continued overnight. Another portion of bromoethane (0.3 g, 2.8 mmol) and triethylamine (10.07 g, 0.7 mmol) were added and the reaction continued for 3 h at room temperature. Water was added and the pH adjusted to about 13 and the mixture was extracted twice with CH$_2$Cl$_2$. The organic layer was dried (MgSO$_4$) and evaporated to give 4.2 g (86%) crude title ester (97% purity according to GLC).

1E. Bromoethane (27.2 g, 0.25 mol) was added during 1 h to a stirred suspension of L-proline (11.5 g, 0.1 mol), potassium carbonate (27.6 g, 0.2 mol), and tris (3,6-dioxaheptyl)amine (TDA-1) (6.5 g, 0.02 mol) in dichloromethane (90 ml) at 25°. The reaction mixture was stirred for another 43 h at 26°–27° C. Water (100 ml) was added and after stirring for a short while at room temperature, the two homogeneous phases were separated. The waterphase was extracted with another portion of dichloromethane (150 ml). The combined organic phases were dried ($MgSO_4$), filtered, and evaporated affording 14.4 g of a yellow liquid.

Distillation of the crude product under reduced pressure gave 6.2 g (48 % yield from L-proline) of a colourless liquid (bp 26°–27° C./0.6 mm Hg), with 99.8% purity according to GLC.

Example 2. Allyl (S)-1-allyl-2-pyrrolidinecarboxylate

L-Proline (21.3 g, 0.185 mol) and $K_2CO_3$ (60.8 g, 0.44 mol) were suspended in 150 ml DMSO. Allyl bromide (36 ml, 0.43 mol) in 50 ml DMSO was added dropwise for 3 h at 0° C. The temperature was allowed to reach room temperature and the stirring was continued overnight. The mixture was poured into 1200 ml aqueous NaCl and extracted twice with $Et_2O$. The organic layer was washed with water, dried ($Na_2SO_4$) and evaporated to give 25.9 g (72%) crude title ester. Chromatography on $SiO_2$ with $iPr_2O$ as eluent gave 17.7 g (49%) title compound having a purity of 95% according to GLC.

MS (EI, 70 eV): m/z (rel.int) 195(M, 1.2%), 110(100%).

Example 3. 4-Fluorobenzyl (R)-1-(4-fluorobenzyl)-2-pyrrolidinecarboxylate

D-proline (9.0 g, 0.078 mol) and $K_2CO_3$ (23.5 g, 0.17 mol) were suspended in 100 ml DMSO and 4-fluorobenzyl bromide (30.2 g, 0.16 mol) in 50 ml DMSO was added dropwise for 3 h at room temperature. The mixture was stirred overnight and poured into 1000 ml ice-water and extracted twice with $Et_2O$. The $Et_2O$ phases were combined, washed with water, dried ($Na_2SO_4$) and evaporated to give 22.6 g (87%) crude title ester.

MS (EI, 70 eV): m/z (rel.int.) 331(M, 0.10%), 178(73%), 109(100%).

Example 4. Cyclopropylmethyl (−)-(S)-1-cyclopropylmethyl-2-pyrrolidinecarboxylate L-Proline (12.5 g, 0.11 mol), $K_2CO_3$ (33.2 g, 0.24 mol) and KI (60 mg) were suspended in 150 ml DMSO. (Cyclopropylmethyl)chloride (20.7 g, 0.23 mol) in 50 ml DMSO was added dropwise for 1 h at 0° C. The temperature was allowed to reach the ambient temperature and the mixture was stirred for 3 days. The mixture was poured into 500 ml ice-water and extracted twice with $Et_2O$. The organic layer was extracted with 0.5M aqueous HCl. The acidic phase was washed with $ET_2O$, made alkaline and extracted with $ET_2O$. Drying ($Na_2SO_4$) and evaporation afforded 6.45 g (27%) essentially pure title ester (>99.7% according to GLC). $[\alpha]_D^{22}=-61°$ (c=0.12, $CHCl_3$).

MS (EI, 70 eV): m/z (rel.int.) 223(M, 0.69%), 124(100%).

Example 5. Methyl (−)-(S)-1-propyl-2-pyrrolidinecarboxylate

5A. Thionyl chloride (65 ml, 0.89 mol) was added dropwise at ice-cooling for 45 min to a solution of L-proline (57.6 g, 0.50 mol) in 500 ml MeOH. The temperature was raised to reflux and after 4 h the solvent was evaporated in vacuo. MeOH was added to the residue and then evaporated repeatedly to give 86 g crude methyl (S)-2-pyrrolidinecarboxylate hydrochloride (99.6% purity by GLC) as a thick syrup. The ester (16.5 g, 0.10 mol) was transferred to a flask containing propionaldehyde (36 ml, 50 mol), 10% Pd/C (1.5 g) and 100 ml MeOH. The mixture was shaken in a Parr apparatus overnight at a hydrogen pressure of 55 psi at room temperature. Filtration and evaporation in vacuo gave 22.0 g of the crude title ester (94% purity by GLC) as a hydrochloride salt, which was used in the aminolysis in Example 11B.

5B. Methyl (S)-2-pyrrolidinecarboxylate hydrochloride (1.65 g, 0.01 mol) was added to a hydrogenation flask containing a mixture of propionaldehyde (2.4 g, 0.04 mol), 5% Pd/C (0.3 g) and 30 ml MeOH. The mixture was shaken an a Parr apparatus at 40 psi hydrogen pressure for 2 h at room temperature. After filtration and evaporation the residue was mixed with 10 ml 2M HCl and 40 ml ice-water and then extracted twice with $ET_2O$. Solid NaCl was added to the aqueous phase which was made alkaline with 20 ml 2M $NH_3$ during addition of ice. Extraction with $Et_2O$ twice, drying ($MgSO_4$) and evaporation afforded 1.8 g of the title compound, which was used directly in Example 11A. $[\alpha]_D^{25}=-85°$ (c=1.3, $CHCl_3$); MS (EI, 70 eV): m/z (rel.int.) 171(M, 1.9%), 112(100%).

Example 6. Methyl (S)-1-ethyl-2-pyrrolidinecarboxylate

6A. Thionyl chloride (65 ml, 0.89 mol) was added dropwise at ice-cooling for 45 min to a solution of L-proline (57.6 g, 0.50 mol) in 500 ml MeOH. The temperature was raised to reflux. After 4 h at reflux the mixture was cooled and the solvent evaporated in vacuo. MeOH was added to the residue and then evaporated repeatedly three times to give 86 g crude methyl (S)-2-pyrrolidinecarboxylate hydrochloride (99.6% purity by GLC) as a thick syrup. The ester (1.65 g, 0.01 mol) was transferred to a flask containing acetaldehyde (2.21 g, 0.05 mol) 10% Pd/C (0.15 g) and 15 ml MeOH. The mixture was shaken in a Parr apparatus at 55 psi hydrogen pressure for 4 h at room temperature, filtered and evaporated to give 2.1 g crude hydrochloride of the title ester. (91% purity by GLC). This material was subjected to aminolysis in Example 7D.

MS (EI, 70 eV): m/z (rel.int.) 157(M, 2.4%), 98(100%).

68. Bromoethane (6.0 g, 55 mmol) was added to a slurry of methyl (S)-2-pyrrolidinecarboxylate hydrochloride (8.3 g, 50 mmol), $K_2CO_3$ (13.8 g, 100 mmol) and triethylamine (0.25 g, 2.5 mmol) in 75 ml $CH_2Cl_2$ at room temperature for 20 min. The mixture was stirred overnight and more bromoethane (1.1 g, 10 mmol) and triethylamine (0.07 g, 0.7 mmol) were added and the temperature raised to 30° C. After stirred overnight another 1.1 g bromoethane was added and the reaction continued for 4 h. Water was added and the pH was adjusted to about 12. After separation the water layer was extracted with $CH_2Cl$. Drying ($MgSO_4$) and evaporation of the organic layers gave 6.6 g (80%) crude title ester.

Example 7. (−)-(S)-1-Ethyl-2-pyrrolidinecarboxamide

7A. A mixture of ethyl (S)-1-ethyl-2-pyrrolidinecarboxylate (6.00 g, 35 mmol) and NaCN (70 mg, 3.5 mmol) in 100 ml 9M ammonia in methanol was heated to 45° C. in a sealed glass flask for 40 h. The mixture was evaporated, the residue dissolved in 250 ml $CH_2Cl_2$ and washed with 100 ml $H_2O$. The aqueous layer was extracted with 200 ml $CH_2Cl_2$. The organic phases were combined, dried ($MgSO_4$) and evaporated to give 4.78 g (96%) of amide with 98% purity. Recrystallization from hexane/$iPr_2O$ 5:1 gave 3.58 g (72%) pure title amide, mp 110°–111° C.

$[\alpha]_D^{20}$=–123° (c=0.8, $CHCl_3$) The enantiomeric purity was determined by chromatography on a chiral GLC column (Chiracil-Val, 25 m) and found to be 99.4% S-isomer. MS (EI, 70 eV): m/z (rel.int.) 142(M, 0.2%), 98(100%), 70(21%).

7B. Ethyl (–)-(S)-1-ethyl-2-pyrrolidinecarboxylate (3.4 g, 0.02 mol) was added to a cooled solution of MeOH (10 ml) and liquid $NH_3$ (10 ml) in a stainless steel reaction bottle containing 3 g of 3 A molecular sieves. The bottle was heated at 50° C. for 20 h. After cooling the solvent was allowed to evaporate. The product was dissolved in dry MeOH, filtered and the filtrate was evaporated under reduced pressure to give the title compound as white crystals in a quantitative yield (2.8 g).

Recrystallization from n-hexane afforded 2.5 g (88%) of the amide, mp 107°–108° C. $[\alpha]_D^{25}$=–119° (c=0.5 MeOH). The enantiomeric purity was determined to 99.7% S-isomer.

7C. Crude ethyl (S)-1-ethyl-2-pyrrolidinecarboxylate (13.6 g, 0.07 mol), NaCN (0.34 g, 7 mmol), 100 ml MeOH and 29 g $NH_3$ was mixed in an autoclave and heated to 50° C. for 64 h. Usual work-up afforded 9.7 g (96%) of the title amide as a white to off-white solid having an enantiomeric purity of 99.3%.

7D. Crude methyl (S)- 1-ethyl-2-pyrrolidinecarboxylate hydrochloride (2.1 g, 0.01 mol; Example 6A) and NaCN (50 mg, 0.001 mol) in 30 ml 9M $NH_3$ in MeOH was heated to 45° C. in a sealed glass flask for 2 days. GLC showed a conversion of 95% and usual work-up afforded 0.9 g (63%) of the title compound.

7E. (S)-1-Ethyl-2-pyrrolidine carboxamide To a solution of (S)-2-pyrrolidine carboxamide (13.2 g, 116 mmol) in ethanol (140 ml) $K_2CO_3$, (17.6 g, 128 mmol) and triethylamine (1.2 ml, 8.6 mmol) were added. The mixture was heated to 30° C. and stirred vigorously. Then ethylbromide (10.4 ml, 138 mmol) was added during 0.5 hours. After 30 hours the mixture was diluted with toluene (50 ml) and washed with water (50 ml). The organic layer was concentrated at reduced pressure. The residue was dissolved in toluene (150 ml) and washed with a small amount of aqueous sodium hydroxide, dried with magnesium sulfate, and evaporated to dryness in vacuo. Yield 10.7 g (65%). MS (EI, 70 ev): M/Z (rel.int.) 142 (M, 0.2%), 98 (100%), 70 (21%).

Example 8. (–)-(S)-Allyl-2-pyrrolidinecarboxamide

8A. Allyl (S)-1-allyl-2-pyrrolidinecarboxylate (17.6 g, 0.090 mol; Example 2) was stirred in 1500 ml 6M ammonia in methanol at room temperature for 5 days. Evaporation gave 14.5 g which were recrystallized from 70 ml $iPr_2O$ to afford 9.4 g (67%) of the title compound; mp 79°–81° C.; $[\alpha]_D^{20}$=–107° C. (c=0.9, $CHCl_3$). MS (EI, 70 eV): m/z (rel.int.) 154(M, 1.7%), 110(100%).

8B. Allyl (S)-1-allyl-2-pyrrolidinecarboxylate (2.5 g, 12.8 mmol; and NaCN (64 mg, 1.3 mmol) in 50 ml 9M ammonia in methanol were stirred at 35° C. for 27 h. GLC showed a complete conversion. After evaporation the residue was dissolved in $Et_2O$ and washed with brine. Drying ($Na_2SO_4$), evaporation and recrystallization gave 1.6 g.(81%) of the title amide identical with the one made in Example 8A.

Example 9. (+)-(R)-1-(4-Fluorbenzyl)-2-pyrrolidine carboxamide

9A. Crude 4-fluorobenzyl (R)-1-(4-fluorobenzyl)-2-pyrrolidinecarboxylate (2.10 g, 6.3 mmol; Example 3) was stirred in 25 ml 4M ammonia in methanol at room temperature for 4 days. After evaporation the residue was dissolved in $Et_2O$ and extracted with 0.5M HCl. The aqueous phase was made alkaline with ammonia and extracted with $Et_2O$ twice. Drying ($Na_2SO_4$) and evaporation gave 1.4 g crystalline material. Recrystallization from $Et_2O$/hexane 1:1 gave 0.87 g (62%) pure title amide, mp 79°–82° C.; $[\alpha]_D^{20}$= +73° (c=0.49, $CHCl_3$);

MS (EI, 70 eV): m/z (rel.int.) 222(M, 0.27%), 178(46%), 109(100%); Anal.calcd. for $C_{12}H_{15}N_2OF$: C, 64.85; H, 6.80; N, 12.60. Found: C, 64.78; H, 6.74; N, 12.59.

9B. (R)-Prolinamide hydrochloride was prepared according to G. Flouret et al. J. Med.Chem. 16 (1973) 1137 in a yield of 64% (lit. 53%); mp 180°–181° C. (lit 178°–180° C.); $[\alpha]_D^{22}$+67° (c=0.80, EtOH) (lit. $[\alpha]_D^{23}$= +69.5° (c=2, EtOH). To a mixture of (R)-prolinamide hydrochloride (4.3 g, 23 mmol) and $K_2CO_3$ (8.3 g, 60 mmol) in 20 ml dry DMSO was added a solution of p-fluorobenzylbromide (4.5 g, 23.5 mmol) in 3 ml DMSO at room temperature. The reaction mixture was stirred overnight, poured into 200 ml of ice-water and extracted twice with $ET_2O$. The organic layer was washed with water, dried ($Na_2SO_4$) and evaporated. The residue was recrystallized from $iPr_2O$ to give 3.0 g (59%) pure title compound, mp 82°–83° C.; $[\alpha]_D^{22}$=+77° (c=0.8, $CHCl_3$) From the mother liquor was obtained another 1.0 g (20%).

Example 10. (–)-(S)-1-Cyclopropylmethyl-2-pyrrolidinecarboxamide

Cyclopropylmethyl (S)-1-cyclopropylmethyl-2-pyrrolidinecarboxylate (6.30 g, 0.028 mol; Example 4) was stirred in 400 ml 4M ammonia in methanol at room temperature for 21 days. Evaporation and extraction according to Example 9 gave 4.0 g (84%) amide. Recrystallization from i-$Pr_2O$ gave pure amide mp 86°–88° C. $[\alpha]_D^{22}$=–93° (c=0.7, $CHCl_3$) .

MS (EI, 70 eV): m/z (rel.int.) 124(100%). Anal.calcd. for $C_9H_{16}N_2O$: C, 61.50; H, 10.23; N, 17.93. Found: C, 61.61; H, 10.22; N, 17.93.

Example 11. (–)-(S)-1-Propyl-2-pyrrolidinecarboxamide

11A. A mixture of methyl (S)-1-propyl-2-pyrrolidinecarboxylate (1.8 g, 0.01 mol; Example 5 ) and NaCN (49 mg, 0.001 mol) in 30 ml 9M ammonia in methanol was heated at 45° C. for 3 days. After evaporation the residue was dissolved in $CH_2Cl_2$ and washed with brine. The aqueous phase was extracted with $CH_2Cl_2$ and the combined organic layers were washed with brine. Drying ($MgSO_4$) and evaporation gave 1.55 g crystalline material, which was recrystallized from hexane to give 1.23 g (79%) pure title compound, mp 110°–112° C. $[\alpha]_D^{22}$=–117° (c=1.2, $CHCl_3$);

MS(CI, $NH_3$): m/z (rel.int.) 157(M+1, 100%), 112(32%). Anal.calcd. for $C_8H_{16}N_2O$: C, 61.50; H, 10.32; N, 17.93. Found: C, 61.61; H, 10.22;N, 17.93.

11B. A mixture of methyl (S)-1-propyl-2-pyrrolidinecarboxylate hydrochloride (22.0 g, 0.1 mol) and NaCN (0.50 g, 0.01 mol) in 300 ml 9M ammonia in methanol was heated at 50° C. for 5 days in an autoclave. Evaporation and usual extractive work-up gave a residue which was recrystallized from hexane to give 10 g (64%) title amide, mp 112°–3° C.

Example 12.
(−)-(S)-2-Aminomethyl-1-ethylpyrrolidine

12A. A mixture of (S)-1-ethyl-2-pyrrolidinecarboxamide (0.50 g, 3.5 mmol) and LiAlH$_4$ (145 mg, 3.9 mmol) was refluxed in 25 ml dry THF overnight. The reaction was quenched by sequential addition of 0.15 ml H$_2$O, 0.15 ml 15% aqueous NaOH and 0.45 ml H$_2$O. The mixture was filtered, dried (MgSO$_4$) and,evaporated. Kugelrohr distillation afforded 0.31 g (69%) of the title amine. $[\alpha]_D^{22}$=−92.4° (c=0.9, CHCl$_3$), $[\alpha]_D^{22}$=−91.4° (c=1.0, DMF). A samle was derivatized with O-methyl mandelic acid chloride and analyzed on capillary GLC and found to be enantiomerically pure (i.e. 98.7% S-isomer).

MS (EI, 70 eV): m/z (rel.int.) 128(M, 1.1%), 98(100%).

12B. (S)-1-ethyl-2-pyrrolidinecarboxamide (0.28 g, 2 mmol) was added portionwise during 3 min to 14 ml of a solution of sodium bis(2-methoxyethoxy)aluminium dihydride (4.8 mmol) in toluene at ambient temperature under N$_2$. Each addition of the amide caused frothing. The reaction mixture was stirred overnight at room temperature under a blanket of N$_2$. A few ml of water was added and the mixture was made acidic with 2M HCl solution and then alkaline with 50% NaOH solution. The aqueous phase was extracted twice,with ether and then twice with methylene chloride. The combined organic phases was dried (MgSO$_4$) and the solvents evaporated in vacuo yielding 240 mg of a colourless oil. The crude title amine was purified by Kugelrohr distillation affording 150 mg (60%) of the desired amine. The optical purity was determined by GC after derivatization with Mosher's acid chloride (S)-(−)-2-methoxy-α-trifluoromethylphenylacetyl chloride) to be >99%.

12C. Bis (2-methoxyethoxy)aluminium dihydride (203.4 g, 0.70 mol, approx. 70% solution in toluene) and toluene (80 ml, dried over molecular sieves A) were added to a three-necked round-bottomed flask. The temperature in the flask was increased to 40° C. and then (S)-1-ethyl-2-pyrrolidinecarboxamide (21.0 g, 0.147 mol, 95% purity on GC) was added spoonwise during 45 min. In order to maintain the temperature at approx. 40° C., cooling was necessary during the addition. The temperature was decreased below 10° C. 55 min after completed addition. Water (500 ml) was added during 15 min and the pH was adjusted to 1 by adding 115 ml concentrated HCl and 100 ml H$_2$O. After extraction, the phases were separated and 200 ml CH$_2$Cl$_2$ were added to the water phase. The pH was subsequently adjusted to 13–14 by adding NaOH (40%, 50 ml). The organic phase was separated and the water phase was extracted with further portions of CH$_2$Cl$_2$ (200+100 ml). The combined organic phases were dried, filtered and concentrated under vacuo to afford 24.8 g crude title product (83%) in an optical purity of >99%.

12D. Sodium borohydride (5.0 g, 0.13 mol) was suspended in 50 ml of dry dioxane. Acetic acid (7.4 g , 0.13 mol) was added dropwise with stirring. The mixture was refluxed overnight (16 h). After cooling the solvent was evaporated in vacuo affording a white precipitate, which was suspended in water. The suspension was made acidic by addition of HCl dropwise. After the gas evolution had subsided the solution was made alkaline with NaOH solution and extracted several times with CH$_2$Cl$_2$. The combined extracts was dried (MgSO$_4$) and evaporated under reduced pressure to give 2.0 g of title product. The crude Material was distilled to afford 1.1 g (65%) of the desired amine. Bp 50°–52°/10 mm Hg. The optical purity was determined after derivatization with trifluoracetyl-L-prolyl chloride using capillary GLC and was found to be 99.5% of the S-enantiomer.

Example 13.
(−)-(S)-1-Allyl-2-aminomethylpyrrolidine

A solution of (S)-1-allyl-2-pyrrolidinecarboxamide (1.0 g, 6.5 mmol) in 5 ml THF was added dropwise to a solution of sodium bis (2-methoxyethoxy) aluminium hydride (3.7 g, 70% solution in toluene, 13 mmol) and 50 ml toluene at 70° C. After heating for 4 h the reaction mixture was quenched with 2M aqueous HCl and washed with Et$_2$O twice. The aqueous phase was made alkaline with 45% NaOH and extracted twice with EtOAc. Kugelrohr distillation gave 270 mg (30%) enantiomerically pure (>99% S-isomer) title amine. Recrystallized as oxalate from aqueous ethanol, mp 133°–135° C.

MS (EI, 70 eV): m/z (rel.int.) 140(M, 0.42%), 110(100%).

Example 14.
(+)-(R)-2-Aminoethyl-1-(4-fluorobenzyl)pyrrolidine

Acetic acid (9.5 g, 0.16 mol) in 20 ml dioxane was added to NaBH$_4$ (6.0 g, 0.16 mol) in 50 ml dioxane. After stirring for 0.5 h at room temperature the mixture was cooled to +5° C. and (R)-1-(4-fluorobenzyl)-2-pyrrolidinecarboxamide (7.0 g, 0.03 mol) in 50 ml dioxane was added. The mixture was stirred 0.5 h at +5° C. and then heated at reflux overnight. After evaporation of the solvent 500 ml ice-water was added and the mixture was extracted twice with CHCl$_3$. Drying (Na$_2$SO$_4$) and evaporation gave 6 7 g enantiomerically pure (>99 5%) title amine $[\alpha]_D^{23}$=+85° (c=0.8, CHCl$_3$). The L-tartrate salt was recrystallized from aqueous ethanol to give 8.8 g (55%, mp 171°–173° C).

MS (EI, 70 eV): m/z (rel.int.) 208(M, 0.20%), 178(48%), 109(100%). Anal.calcd. for C$_{20}$H$_{29}$FN$_2$O$_{12}$0.5 H$_2$O: C, 46.42; H, 5.84; N, 5.41. Found: C, 46.36; H, 5.62; N, 5.34.

Example 15.
(−)-(S)-2-Amninomethyl-1-(cyclopropylmethyl)pyrrolidine

A mixture of (S)-1-cyclopropylmethyl-2-pyrrolidinecarboxamide (4.0 g, 24 mmol) and lithium aluminium hydride (0.99 g, 26 mmol) in 50 ml THF was refluxed overnight. After sequential addition of 1 ml H$_2$O, 1 ml 15% aqueous NaOH and 3 ml H$_{20}$ the mixture was filtered, washed with Et$_2$O and evaporated to give 3.7 g crude title product. Kugelrohr distillation gave 2.4 g (65%) amine, bp 105°–110° C./18 mm Hg. $[\alpha]_D^{22}$=−67° (c= 0.8, CHCl$_3$).

MS (EI, 70 eV): m/z (rel.int.) 154(M, 0.17%), 124(100%).

Example 16.
(−)-(S)-2-Aminomethyl-1-propylpyrrolidine 16A. (S)-1-propyl-2-pyrrolidinecarboxamide (6.0 g, 0.038 mol) in 100 ml dry THF was added dropwise under N$_2$ at ice-cooling to a stirred solution of lithium aluminium hydride (1.7 g, 0.046 mol) in 150 ml dry THF. After the addition the temperature was raised to reflux which was maintained overnight. The mixture was cooled and 11 ml saturated aqueous Na$_2$SO$_4$ was added dropwise. Filtration, washing of the filter cake with THF and evaporation of the solvent gave a residue, which was distilled to give 4.2 g (78%) pure title amine, bp 68° C./10 mm Hg $[\alpha]_D^{22}$=−93° (c=0.9, CHCl$_3$). The enantiomeric purity was 97% of S-isomer.

MS (EI, 70 eV): m/z (rel.int.) 142(M, 0.2%), 112(100%).

16B. (S)-1-Propyl-2-pyrrolidinecarboxamide (430 mg, 2.8 mmol) was added portionwise to 2.1 ml of bis (2-methoxyethoxy)aluminium dihydride (70% in toluene, 8.1 mmol) and 10 ml toluene under $N_2$ at room temperature. The mixture was stirred overnight at room temperature. After cooling 20 ml 2M HCl was added. The mixture was washed with Et2O, made alkaline with 45% NaOH and saturated with solid NaCl. Extraction with EtOAc, drying (MgSO$_4$) and evaporation afforded an oil which was subjected to Kugelrohr distillation to give 250 mg (63%) enantiomerically pure title amine (>99.5%).

We claim:

1. An (R)- or (S)-isomer of the compound of the formula III with at least 95% optical purity

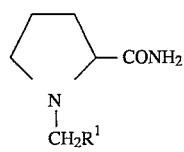
(III)

wherein $R^1$ is a lower alkyl, lower alkenyl or lower alkynyl group, a cycloalkyl group, or a group $(CH_2)_m$ Ph, wherein m is 0–3 and Ph is an unsubstituted or substituted phenyl group with one or more substituents selected from the group consisting of halo, trifluoromethyl, lower alkyl, hydroxy, methoxy, ethoxy and methylenedioxy or a salt thereof.

2. A compound according to the formula III with at least 95% optical purity,

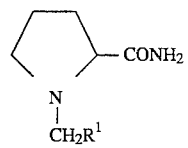
(III)

wherein $R^1$ is methyl, ethyl, cyclopropyl, vinyl or halophenyl, or salt thereof.

3. The compound according to claim 2, which is (S)-1-ethyl-2-pyrrolidine carboxamide.

4. The compound according to claim 2, which is (S)-1-propyl-2-pyrrolidine carboxamide.

5. The compound according to claim 2, which is (R)-1-(4-fluorobenzyl)-2-pyrrolidine carboxamide.

6. An (R)- or (S)-isomer of the compound of the formula II with at least 95% optical purity,

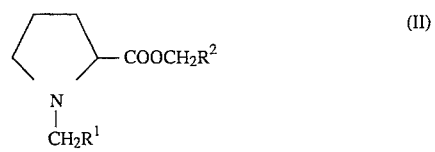
(II)

wherein $R^1$ and $R^2$ are the same or different and represent a hydrogen atom, a lower alkyl, lower alkenyl or lower alkynyl group, a cycloalkyl group, or a group $(CH_2)_m$ Ph, wherein m is 0–3 and Ph is an unsubstituted or substituted phenyl group with one or more substituents selected from the group consisting of halo, trifluoromethyl, lower alkyl, hydroxy, methoxy, ethoxy and methylenedioxy, with the proviso that when $R^2$ is hydrogen then $R^1$ and $R^2$ are different and with the further proviso that when $R^2$ is hydrogen and $R^1$ is a group $(CH_2)_m$Ph wherein m is O, then Ph is unsubstituted or substituted with one or more substituents selected from the group consisting of halo, trifluoromethyl, hydroxy, lower alkyl, ethoxy and methylenedioxy; or a salt thereof.

7. A compound according to claim 6, wherein $R^1$ is methyl, ethyl, cyclopropyl, vinyl or halophenyl.

8. A compound according to claim 7, wherein $R^1$ is 4-fluorophenyl.

* * * * *